Feb. 11, 1964 C. FISCHER Plant Pat. 2,363
GLADIOLUS PLANT
Filed Dec. 18, 1962
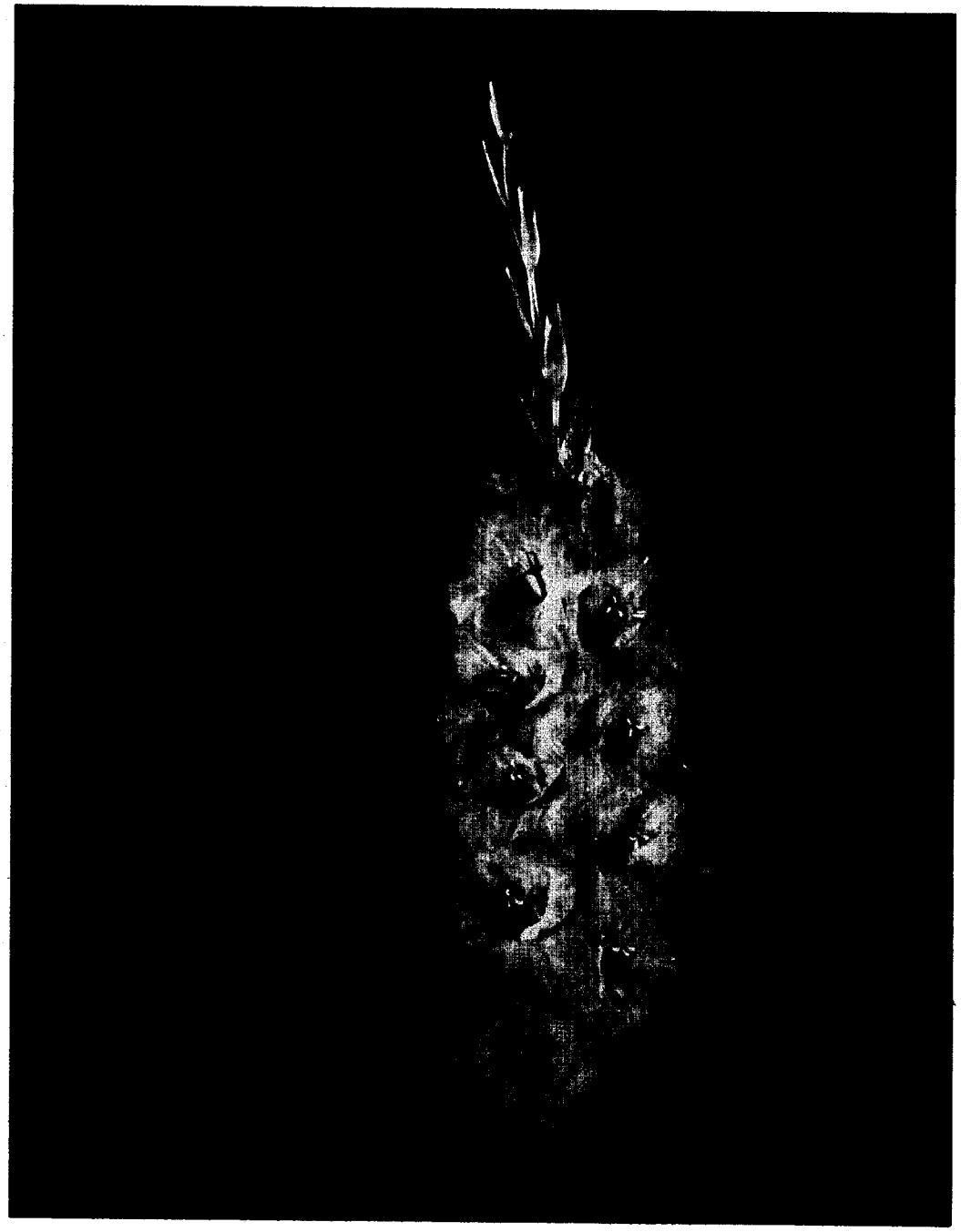
Inventor.
Carl Fischer
By: Robb & Robb
Attorneys.

United States Patent Office

Plant Pat. 2,363
Patented Feb. 11, 1964

2,363
GLADIOLUS PLANT

Carl Fischer, St. Charles, Minn., assignor to Imperial Flowers Limited, Leamington, Ontario, Canada, a corporation of Canada Filed Dec. 18, 1962, Ser. No. 245,632
1 Claim. (Cl. Plt.—85)

The present invention relates to a new and distinct variety of gladiolus plant which was originated by me by crossing the variety "Royal Stewart" (Plant Patent No. 1,339) with an unnamed and unpatented seedling of unidentified parentage, the variety "Royal Stewart" being the seed parent and the unnamed seedling being the pollen parent. This cross was made by me by manual cross-pollination in my breeding fields at St. Charles, Minnesota, as a part of a breeding program seeking to obtain new and improved gladiolus varieties.

As the result of this breeding, I have produced a new gladiolus variety which is endowed with a unique combination of outstanding features which distinguishes it from its parents, as well as from all other varieties of which I am aware, as evidenced by the following characteristics which are present therein:

(1) A tall habit of plant growth when grown in the field;

(2) A double row arrangement of the florets on the flower stems;

(3) A flower habit which is characterized by the showing of color by nearly all buds, with specks of color breaks on some petals; and (4) A distinctive, brilliant Geranium Lake general tonality of the flowers.

My new variety resembles the seed parent "Royal Stewart" more than any other variety, but differs principally therefrom by a healthier habit, somewhat smaller size, more brilliant flower color and the breaking of small specks of color on some of the flower petals.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminonogy in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Vigorous; propagates readily; average height ranges from about 58 inches to 60 inches.

Blooming habit: Mid-season bloomer in the Northern latitudes of the United States; comes into bloom from large bulbs in about 80 days; bears from 20 to 22 buds on each spike, with 9 or 10 buds opening at one time.

Stems: Tall; straight.

*Diameter at base.*—From ½ inch to ⅝ inch.

*Color (just above bulb).*—Reddish brown.

Foliage: Very stiff; upright; leaves average from about 36 inches to 40 inches tall and about 1¾ inches wide. Color—deep green.

Disease resistance: Especially resistant to Septoria leaf spot, but only average resistance to Fusarium yellows and Sclerotina dry rot, as determined by comparison with other varieties grown in my fields near St. Charles, Minnesota, in irrigated black loam soil.

Corms (bulbs): Round; plump; average diameter about 2 inches; well-husked, with husk being thick and coarse and having a purplish cast. Color of flesh—tinted from Brick Red, Plate 016/1 to Brick Red, Plate 016/3.

*Flower*

Spike: Tall; straight; bears from 20 to 22 buds, with 9 or 10 florets opening at once and with 8 or 9 buds showing color; almost all the buds are either open or show color.

Bud:

*Size.*—From 3 inches to 3½ inches long when opening.

*Opening.*—Almost all the buds are either open or show color; opens better than most red-color gladiolus varieties.

Flower:

*Arrangement.*—Florets are arranged formally in a double row on the stems and all face in the same direction.

*Size.*—Lower florets average from 5 inches to 5½ inches in diameter when permitted to bloom on the plant, with upper florets being progressively smaller.

*Form.*—Formal; wide open; slightly ruffled; florets are somewhat cupped.

*Keeping qualities.*—Keeps better than most red-color gladiolus varieties.

Petals:

*Shape.*—Round; slightly ruffled.

*Size.*—Upper petals—about 2¾ inches wide. Inner petals—about 2½ inches wide.

*Aspect.*—Somewhat heavier than average substance; smooth and firm surface.

*Fragrance.*—None.

*Color.*—Basically Geranium Lake, Plate 20, with inner petals shading to Geranium Lake, Plate 20/1, and reverse of lip petals shading to Geranium Lake, Plate 20/3; sometimes there are white streaks and/or flecks on some florets which appear on both the front and reverse of the petals, but usually these markings do not extend entirely through to the opposite side of the petal.

*Reproductive Organs*

Stamens: Color—Erythrite Red, Plate 0027.

Pistil: Color—Creamy white.

I claim:

A new and distinct variety of gladiolus plant, substantially as herein shown and described, characterized particularly as to novelty by the unique combination of a tall habit of plant growth, a double row arrangement of the florets on the flower stems, a habit of nearly all buds showing color, with specks or streaks of white color breaking on some petals, and a distinctive, brilliant Geranium Lake general color tonality of the flowers.

No references cited.